US008558062B2

(12) United States Patent
Benson et al.

(10) Patent No.: US 8,558,062 B2
(45) Date of Patent: Oct. 15, 2013

(54) HIGH OLEIC IMIDAZOLINONE RESISTANT SUNFLOWER

(75) Inventors: Robert M. Benson, Ellsworth, WI (US); James T. Gerdes, Breckenridge, MN (US); Guillermo Nestor Pozzi Jauregui, Buenos Aires (AR); Maria Magdalena Lopez Olaciregui, Santa Fe (AR)

(73) Assignee: Dow AgroSciences, LLC., Indianapolis, IN (US)

( * ) Notice: Subject to any disclaimer, the term of this patent is extended or adjusted under 35 U.S.C. 154(b) by 1191 days.

(21) Appl. No.: 11/992,825

(22) PCT Filed: Sep. 28, 2006

(86) PCT No.: PCT/US2006/038034
§ 371 (c)(1), (2), (4) Date: Mar. 28, 2008

(87) PCT Pub. No.: WO2007/038738
PCT Pub. Date: Apr. 5, 2007

(65) Prior Publication Data
US 2010/0168452 A1    Jul. 1, 2010

Related U.S. Application Data

(60) Provisional application No. 60/721,181, filed on Sep. 28, 2005.

(51) Int. Cl.
*A01H 1/00* (2006.01)
*A01H 4/00* (2006.01)
*A01H 5/00* (2006.01)
*A01H 5/10* (2006.01)
*A23L 1/00* (2006.01)

(52) U.S. Cl.
USPC ........... 800/300; 435/416; 426/489; 800/260; 800/265; 800/322

(58) Field of Classification Search
None
See application file for complete search history.

(56) References Cited

U.S. PATENT DOCUMENTS

| | | | |
|---|---|---|---|
| 4,627,192 A | 12/1986 | Fick | |
| 5,276,264 A | 1/1994 | Heaton et al. | |
| 6,388,113 B1 | 5/2002 | Martinez Force et al. | |
| 6,956,156 B2* | 10/2005 | Gerdes et al. | 800/322 |
| 2004/0187180 A1 | 9/2004 | Gerdes et al. | |

OTHER PUBLICATIONS

PCT International Search Report and Written Opinion for International Application No. PCT/US2006/038034, mailed Aug. 20, 2007.
PCT International Preliminary Report on Patentability for International Application No. PCT/US2006/038034, dated Apr. 1, 2008.

* cited by examiner

*Primary Examiner* — David H Kruse
(74) *Attorney, Agent, or Firm* — Marcia I. Rosenfeld

(57) ABSTRACT

A sunflower seed having imidazolinone resistance and an oleic acid content of greater than 85 percent is provided. Sunflower cultivars designated E83329, OI1601A, OI2653R, and OI1601B and having high oleic acid and imidazolinone resistance, plants and seeds of the E83329, OI1601A, OI2653R, and OI1601B sunflower cultivars, methods for producing a sunflower plant produced by crossing the E83329, OI1601A, OI2653R, or OI1601B cultivar with itself or with another sunflower plant, and hybrid sunflower seeds and plants produced by crossing the E83329, OI1601A, OI2653R, or OI1601B cultivar with another sunflower line or plant are also provided.

32 Claims, No Drawings

HIGH OLEIC IMIDAZOLINONE RESISTANT SUNFLOWER

PRIORITY CLAIM

This application claims the benefit of U.S. Provisional Application No. 60/721,181 filed on Sep. 28, 2005.

TECHNICAL FIELD

This invention relates to a novel sunflower (*Helianthus* sp.) plant, to products obtained from the novel plant, and to methods of producing the sunflower products.

BACKGROUND

Sunflower is one of the few crop species that originated in North America. It was probably domesticated by Native American tribes around 1000 B.C. The first Europeans observed sunflower cultivated in many places across North America, from southern Canada to Mexico. Sunflower was probably first introduced to Europe through Spain, eventually reaching Russia where it was extensively cultivated. Selection for high oil began in Russia in 1860 and resulted in oil content increasing from 28 percent to 50 percent. These high-oil lines from Russia were introduced into the United States after World War II. The later discovery of the male-sterile and restorer gene system made hybrids feasible and increased commercial interest in the crop. Production of sunflowers subsequently rose dramatically in the Great Plains states as marketers found new niches for the seeds as an oil crop, a birdseed crop, and as a human snack food.

The cultivated sunflower (*Helianthus annuus* L.) is a major worldwide source of vegetable oil. In the United States, the major sunflower producing states are the Dakotas, Minnesota, Kansas, Colorado, Nebraska, Texas and California, although most states have some commercial acreage. Sunflower oil production in the United States was 2.26 million pounds in 2003. Non-oil production was 406,000 pounds. Non-oil sunflowers averaged 1,256 pounds per acre in 2003, while oil sunflowers had an average yield of 1,206 pounds per acre in 2003.

Sunflowers are considered oilseeds, along with cottonseed, soybeans and canola and the growth of sunflower as an oilseed crop has rivaled that of soybean. The oil accounts for 80 percent of the value of the sunflower crop, as contrasted with soybean, which derives most of its value from the meal. Sunflower oil is generally considered a premium oil because of its light color, high level of unsaturated fatty acids, lack of linolenic acid, bland flavor and high smoke points. The primary fatty acids in the oil are oleic and linoleic with the remainder consisting of palmitic and stearic saturated fatty acids.

Non-dehulled or partly dehulled sunflower meal has been substituted successfully for soybean meal in isonitrogenous (equal protein) diets for ruminant animals, as well as for swine and poultry feeding. Sunflower meal is higher in fiber, has a lower energy value and is lower in lysine but higher in methionine than soybean meal. Protein percent of sunflower meal ranges from 28 percent for non-dehulled seeds to 42 percent for completely dehulled seeds.

In addition to its use in food and food products for humans and animals, sunflower oil also has industrial uses. It has been used in paints, varnishes and plastics because of good semi-drying properties without the color modification associated with oils high in linolenic acid. It has also been used in the manufacture of soaps, detergents and cosmetics. The use of sunflower oil (and other vegetable oils) as a pesticide carrier, and in the production agrichemicals, surfactants, adhesives, fabric softeners, lubricants and coatings has been explored. Considerable work has also been done to explore the potential of sunflower as an alternate fuel source in diesel engines because sunflower oil contains 93 percent of the energy of U.S. Number 2 diesel fuel (octane rating of 37). More recently, sunflower oil has been proposed as a source of hydrogen for hydrogen fuel cells (BBC News, Aug. 26, 2004).

Sunflower is an annual, erect, broadleaf plant with a strong taproot and a prolific lateral spread of surface roots. Stems are usually round early in the season, angular and woody later in the season, and normally unbranched. The sunflower head is not a single flower (as the name implies) but is made up of 1,000 to 2,000 individual flowers joined at a common receptacle. The flowers around the circumference are ligulate ray flowers without stamens or pistils; the remaining flowers are perfect flowers with stamens and pistils. Anthesis (pollen shedding) begins at the periphery and proceeds to the center of the head. Since many sunflower varieties have a degree of self-incompatibility, pollen movement between plants by insects is important, and bee colonies have generally increased yields.

The development of a cytoplasmic male-sterile and restorer system for sunflower has enabled seed companies to produce high-quality hybrid seed. Most of these have higher yields than open-pollinated varieties and are higher in percent oil. Performance of varieties tested over several environments is the best basis for selecting sunflower hybrids. The choice should consider yield, oil percent, maturity, seed size (for non-oilseed markets), and lodging and disease resistance.

As a crop, sunflower yields are reduced, but rarely eliminated, by weeds, which compete with sunflower for moisture and nutrients and occasionally for light. Sunflower is a strong competitor with weeds, especially for light, but does not cover the ground early enough to prevent weed establishment. Therefore, early season weed control is essential for good yields; successful weed control should include a combination of cultural and chemical methods. Almost all North American sunflower plantings are cultivated and/or harrowed for weed control, and over ⅔ are treated with herbicides.

The imidazolinones are a class of herbicides that control a broad spectrum of weeds at low rates and are used throughout the world in legumes, cereals, forests, and plantation crops. These herbicides are widely used, not only because of their efficacy, but also because of their low mammalian toxicity and low environmental impact. The availability of imidazolinone-resistant crops offers many benefits and advantages to the grower by allowing the development of a very flexible weed management program. Because of the broad-spectrum activity and flexible application techniques of the imidazolinones, a weed management program that utilizes a resistant crop can be based on the weeds that need to be controlled with less concern of the relative selectivity of the herbicide. Imidazolinone-resistant crops thus can be an effective weed management tool.

The features of commercially competitive plant varieties generally include more than high yield with excellent standability. While yield is the single most critical input that affects the crop producer's profit, producers expect consistency of yield from year to year, disease resistance, other value-added traits and, more recently, herbicide resistance. The addition of herbicide resistance has created both opportunities as well as tremendous challenges in production agriculture.

References: Putnam, et al. 1990, *Sunflower in Alternative Field Crops Manual*, University of Wisconsin-Extension, Cooperative Extension; University of Minnesota: Center for Alternative Plant & Animal Products; Minnesota Extension Service; M. Boland and J. Stroade 2004, *Sunflower Industry Profile*, Department of Agricultural Economics, Kansas State University; Agricultural Marketing Resource Center; Stephen Duke, Ed., 1996, *Herbicide-Resistant Crops. Agricultural, Environmental, Economic, Regulatory, and Technical Aspects*, CRC Press; U.S. Pat. No. 4,627,192; U.S. Pat. No. 5,276,264; and U.S. Pat. No. 6,388,113.

The foregoing examples of the related art and limitations related therewith are intended to be illustrative and not exclusive. Other limitations of the related art will become apparent to those of skill in the art upon a reading of the specification.

BRIEF SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

It is an aspect of the present invention to provide a hybrid sunflower seed that has a total oleic acid content of at least 85.2 percent and has resistance to imidazolinones.

It is another aspect of the present invention to provide new sunflower plants that can be used efficiently to produce parent lines and hybrids possessing desirable agronomic traits in combination with high oleic acid content.

It is yet another aspect of the present invention to provide a method for producing a hybrid sunflower that is resistant to imidazolinones.

In accomplishing the foregoing aspects, there has been provided, in accordance with the present invention, a sunflower seed having an oleic acid content of greater than 85.2 percent and tolerance to imidazolinone.

In accordance with yet another aspect of the present invention, there has been provided a sunflower variety that has a total oleic acid content of at least 85.2 percent and has resistance to imidazolinones.

Other aspects, features, and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

In the description and examples that follow, a number of terms are used herein. In order to provide a clear and consistent understanding of the specification and claims, including the scope to be given such terms, the following definitions are provided:

ALS inhibitor. As used herein, the "ALS inhibitor" means any herbicidally effective form of sulfonylureas, triazolopyrimidine sulfonamides, imidazolinones or heteroaryl ethers including any salt thereof.

Allele. An "allele" is any of one or more alternative forms of a gene, all of which alleles relate to one trait or characteristic. In a diploid cell or organism, the two alleles of a given gene occupy corresponding loci on a pair of homologous chromosomes.

Backcrossing. "Backcrossing" is a process in which a breeder repeatedly crosses hybrid progeny back to one of the parents, for example, a first generation hybrid $F_1$ with one of the parental genotypes of the $F_1$ hybrid.

Commercially acceptable. The term "commercially acceptable" means a sunflower variety or hybrid having a grain yield of greater than 2000 pounds per acre over at least two years and ten environments.

FAME analysis. "Fatty Acid Methyl Ester (FAME) analysis" is a method that generates accurate quantification of the fatty acids that make up complex lipid classes.

Imidazolinone resistance (Imi). Resistance and/or tolerance is conferred by one or more genes that alter acetolactate synthase (ALS), also known as acetohydroxy acid synthase (AHAS), allowing the enzyme to resist the action of imidazolinone.

Oil content. Oil content is measured as percent of the whole dried seed and is characteristic of different varieties. It can be determined using various analytical techniques such as NMR, NIR, and Soxhlet extraction.

Oleic acid content. Oleic acid is a monounsaturated fatty acid with the chemical formula $C_{18}H_{34}O_2$. Its IUPAC name is cis-9-octadecenoic acid but it is commonly referred to as C18:1. Oleic acid content refers to the percent of the total fatty acid fraction of sunflower oil that consists of C18:1.

Percent oleic acid (OLE). Percent oil of the seed that is oleic acid.

Percent of total fatty acids. The percent of total fatty acids is determined by extracting a sample of oil from seed, producing the methyl esters of fatty acids present in that oil sample and analyzing the proportions of the various fatty acids in the sample using gas chromatography. The fatty acid composition can also be a distinguishing characteristic of a variety.

Protein content. Protein content is measured as percent of whole dried seed and is characteristic of different varieties. This can be determined using various analytical techniques such as MR and Kjeldahl.

Resistance to lodging. Resistance to lodging measures the ability of a variety to stand up in the field under high yield conditions and severe environmental factors. A variety can have good (remains upright), fair, or poor (falls over) resistance to lodging. The degree of resistance to lodging is not expressed under all conditions but is most meaningful when there is some degree of lodging in a field trial.

Single Gene Converted (Conversion). Single gene converted (conversion) plant refers to plants that are developed by a plant breeding technique called backcrossing, wherein essentially all of the desired morphological and physiological characteristics of a variety are recovered in addition to the single gene transferred into the variety via the backcrossing technique or via genetic engineering.

Total Saturated (TOTSAT). Total percent oil of the seed of the saturated fats in the oil including C12:0, C14:0, C16:0, C18:0, C20:0, C22:0 and C24.0.

Mean Yield. Mean yield of all sunflower entries grown at a given location.

Yield. Greater than 10 percent above the mean yield across ten or more locations.

Check Average. The average for one or more check varieties or hybrids in a given location.

Prior to the instant invention, a sunflower variety has never been developed having both high oleic acid oil and imidazolinone resistance combined into one sunflower genotype. These traits have not previously been combined in any commercial or wild-type sunflower. Having both traits in one sunflower variety substantially expands the utility of the crop by providing the highly desirable high oleic acid oil and greater flexibility in weed control.

All crop species are grown for the purpose of harvesting some product of commercial significance. Enhancement of productivity or yield of that product is a major goal of most plant breeding programs. The highest priority in most sunflower cultivar development programs is increasing seed yield. Seed yield is a quantitative character controlled by many genes and strongly influenced by the environment. The heritability of yield is the lowest and the most variable of the major agronomic traits considered in cultivar development, with heritability estimates ranging from 3 to 58 percent. Yield is an example of a quantitative character that breeders attempt to improve beyond the level of that present in current cultivars. Disease resistance is required in most cases to protect the yield potential of a cultivar.

It is a difficult challenge to incorporate an herbicide-resistant or -tolerant trait into high yielding cultivars. The difficulty is increased by several orders of magnitude if a breeder attempts to combine the herbicide resistance with high oleic acid oil into one cultivar. For a plant breeder to find a cultivar with sufficient merit (e.g., high yielding) to be increased and commercially distributed, it is necessary to make many crosses and grow thousands of experimental genotypes. The evaluation of so many genotypes is a huge task, and consumes an enormous amount of the plant breeder's time and budget. In some instances, it can take a decade or more from the time the original cross is made to the time when a commercially viable genotype is identified.

The effectiveness of selecting for genotypes with the traits of interest (e.g., high yield, herbicide resistance, high oleic acid oil) in a breeding program will depend upon: 1) the extent to which the variability in the traits of interest of individual plants in a population is the result of genetic factors and is thus transmitted to the progenies of the selected genotypes; and 2) how much the variability in the traits of interest (yield, herbicide resistance, high oleic acid oil) among the plants is due to the environment in which the different genotypes are growing. The inheritance of traits ranges from control by one major gene whose expression is not influence by the environment (i.e., qualitative characters) to control by many genes whose effects are influenced by the environment (i.e., quantitative characters). Breeding for quantitative traits is further characterized by the fact that: 1) the differences resulting from the effect of each gene are small, making it difficult or impossible to identify them individually; 2) the number of genes contributing to a character is large, so that distinct segregation ratios are seldom, if ever, obtained; and 3) the effects of the genes may be expressed in different ways based on environmental variation. Therefore, the accurate identification of transgressive segregants or superior genotypes with the traits of interest is extremely difficult and its success is dependent on the plant breeder's ability to minimize the environmental variation affecting the expression of the quantitative character in the population. The likelihood of identifying a transgressive segregant is greatly reduced as the number of traits combined into one genotype is increased. For example, if a cross is made between cultivars differing in three complex characters, such as yield, herbicide resistance and high oleic acid oil, it is extremely difficult to recover simultaneously by recombination the maximum number of favorable genes for each of the three characters into one genotype. Consequently, all the breeder can generally hope for is to obtain a favorable assortment of genes for the first complex character combined with a favorable assortment of genes for the second character into one genotype in addition to an herbicide-resistant gene.

The methods used in cultivar development programs and their probability of success are dependent on the number of characters to be improved simultaneously, such as, seed yield, disease resistance, and herbicide-resistant/tolerant traits. The proportion of desired individuals for multiple characters in a population is obtained by multiplying together the proportion of desired individuals expected in the population for each character to be improved. This assumes that the characters are inherited independently, i.e., are not genetically linked.

These principles can be applied not only to traditionally bred lines, but also to lines having one or more transgenes. Whether combining desirable traditional and transgenic traits via hybridization of transgenic lines or cotransformation of multiple genes into one line, the combined effect on yield are likely to be multiplicative. The likelihood of identifying a line with a suitable combination of traits is further reduced when considering the potential effects of a transgene on the regulation of metabolism within a plant. For example, one can consider the potential effect of genes conferring resistance to imidazolinones. The gene conferring this trait is a gene encoding a mutant acetolactate synthase (ALS) enzyme. The ALS gene affects closely related biochemical reactions in the synthesis of amino acids.

Acceptable lines have background genotypes that compensate for or are mainly unaffected by the perturbations caused by the introduced gene. When lines with acceptable herbicide resistance are combined by breeding with lines with high oleic oil, the background genotypes that have adjusted to the introduced or mutant genes are combined, and new genotypes must be selected. The frequency of genotypes with suitable yield will be reduced accordingly. Therefore, it is an extremely difficult hurdle to combine herbicide resistance with high yield and a high oleic acid content in a given sunflower variety or hybrid. Unexpectedly, the traits of imidazolinone resistance with high oleic acid content have been combined in a commercially acceptable cultivar in the present invention. Once these traits have been combined in a variety, then the traits can be transferred to other genetic backgrounds.

DETAILED DESCRIPTION OF THE INVENTION

Applicants have made a deposit of at least 2500 seeds of inbred sunflower plant OI1601A with the American Type Culture Collection (ATCC), Manassas, Va. 20110 USA under ATCC Accession No. PTA-9470.

Applicants have made a deposit of at least 2500 seeds of inbred sunflower plant OI1601B with the American Type Culture Collection (ATCC), Manassas, Va. 20110 USA under ATCC Accession No. PTA-9471.

Applicants have made a deposit of at least 2500 seeds of inbred sunflower plant E83329 with the American Type Culture Collection (ATCC), Manassas, Va. 20110 USA under ATCC Accession No. PTA-9473.

Applicants have made a deposit of at least 2500 seeds of inbred sunflower plant OI2653 with the American Type Culture Collection (ATCC), Manassas, Va. 20110 USA under ATCC Accession No. PTA-9472.

The seeds deposited with the ATCC on Sep. 8, 2008, were taken from a deposit maintained by Agrigenetics, Inc., d/b/a Mycogen Seeds, since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant(s) will maintain and make this deposit available to the public pursuant to the Budapest Treaty.

EXAMPLES

The following examples are provided to further illustrate the present invention and are not intended to limit the invention beyond the limitations set forth in the appended claims.

Example 1

Sunflower Hybrid E83329 Having High Oleic Acid Content and Imidazolinone Resistance One example of imidazolinone resistance and high oleic acid content is sunflower cultivar E83329. E83329 was developed through plant breeding and is stable and uniform. It is a high oleic sunflower that is resistant to imidazolinones. Some of the criteria used to select in various generations include: seed yield, lodging resistance, emergence, disease tolerance and maturity. The hybrid has shown uniformity and stability, as described in the following variety description information. The parent lines have been self-pollinated a sufficient number of generations with careful attention to uniformity of plant type. The hybrid has been increased with continued observation for uniformity. E83329 has the following morphologic and other characteristics.

TABLE 1

| Plant: | |
| --- | --- |
| Height: | 80 inches |
| Number of leaves: | 28 |
| Leaf shape: | Cordate |
| Leaf length: | 11 inches |
| Leaf width: | 10.7 inches |
| Leaf margin indentation: | Intermediate |
| Leaf Attitude: | Descending |
| Days to Flower: | 68 |
| Days to Maturity: | 98 |
| Ray flower color: | Yellow |
| Pappi: | Green |
| Head diameter: | 7 inches |
| Head shape: | Convex |
| Head Attitude: | Descending |
| Seed Number per head: | 1675 |
| Seed weight (g/200): | 10 |
| Harvest moisture (percent): | 10.6 |
| Yield (lbs/acre): | 2910 |
| Percent oil: | 41 |
| Oil Profile: | |
| Oleic: | 86.9 percent |
| C16:0: | 4.05 percent |
| C16:1: | 0.18 percent |
| C18:0: | 2.93 percent |
| C18:2: | 3.01 percent |
| Saturated: | 8.89 percent |
| Imidazolinone resistance: | Excellent |

In Table 2 that follows, select characteristics of E83329 are compared with commercial variety 7350.

TABLE 2

| Trait | E83329 | 7350 |
| --- | --- | --- |
| Days to Flower | 68 | 64 |
| Days to Maturity | 98 | 96 |
| Height | 80 inches | 73 inches |
| Number of Leaves | 28 | 24 |
| Head Diameter | 7 inches | 8 inches |
| Seed No. per Head | 1675 | 1822 |
| Seed Weight (g/200) | 10 | 10 |
| Yield (lbs/acre) | 2910 | 3034 |

In Table 3 that follows, the oil profiles of E83329 and commercial variety 7350 are compared.

TABLE 3

| Oil Trait | E83329 | 7350 |
| --- | --- | --- |
| Total Percent Oil | 41 percent | 45.2 percent |
| Percent Oleic | 86.9 | 87.4 |
| Percent C16:0 | 4.05 | 3.77 |
| Percent C16:1 | 0.18 | 0.15 |
| Percent C18:0 | 2.93 | 3.11 |
| Percent C18:2 | 3.01 | 2.93 |
| Percent Saturated | 8.89 | 8.62 |

In Table 4 that follows, the imidazolinone resistances of E83329 and commercial variety 7350 are compared using a scale of 1 to 9 where 1 is excellent resistance and 9 is poor resistance. Column 1 shows the dosage of herbicide applied and the time after application at which resistance was measured. IMI is imidazolinone herbicide, 1×IMI is one times the standard dosage of imidazolinone and so on.

TABLE 4

| Imidazolinone Resistance | E83329 | 7350 |
| --- | --- | --- |
| 1 week after spray | | |
| 1X IMI | 2.0 | 9.0 |
| 2X IMI | 3.0 | 9.0 |
| 3X IMI | 3.5 | 9.0 |
| 3 weeks after spray | | |
| 1X IMI | 1.0 | 9.0 |
| 2X IMI | 1.0 | 9.0 |
| 3X IMI | 1.0 | 9.0 |

In Table 5 that follows, the FAME analysis of E83329 is compared with that of commercial variety 7350. Each FIGURE is the percent of total fatty acid oil.

TABLE 5

| Oil Profile | E83329 | 7350 |
| --- | --- | --- |
| C14:0 | 0.06 | 0.05 |
| C16:0 | 4.05 | 3.77 |
| C16:1 | 0.18 | 0.15 |
| C18:0 | 2.93 | 3.11 |
| C18:1 | 86.90 | 87.42 |
| C18:2 | 3.01 | 2.93 |
| C18:3 | 0.09 | 0.08 |
| C20:0 | 0.35 | 0.34 |
| C20:1 | 0.32 | 0.33 |
| C20:2 | 0.01 | 0.01 |
| C22:0 | 1.10 | 0.98 |
| C24:0 | 0.40 | 0.36 |
| C24:1 | 0.01 | 0.01 |
| TOTSAT | 8.89 | 8.62 |

Example 2

Sunflower Cultivar OI1601a Having Imidazolinone Resistance and High Oleic Acid Content A second example of imidazolinone resistance and high oleic acid content is sunflower cultivar OI1601A. OI1601A was developed through plant breeding and is stable and uniform. It is a high oleic sunflower that is resistant to imidazolinones. Some of the criteria used to select in various generations include: seed yield, lodging resistance, emergence, disease tolerance and maturity. The cultivar has shown uniformity and stability, as described in the following variety description information. It has been self-pollinated a sufficient number of generations with careful attention to uniformity of plant type. The cultivar has been increased with continued observation for uniformity. OI1601A has the following morphologic and other characteristics.

TABLE 6

| Plant: | |
|---|---|
| Height: | 57 inches |
| Number of leaves: | 29 |
| Leaf shape: | Cordate |
| Leaf length: | 10.6 inches |
| Leaf width: | 10.2 inches |
| Leaf margin indentation: | Intermediate |
| Leaf Attitude: | Descending |
| Days to Flower: | 68 |
| Days to Maturity: | 95 |
| Ray flower color: | Yellow |
| Pappi: | Green |
| Head diameter: | 7 inches |
| Head shape: | Convex |
| Head Attitude: | Descending |
| Percent oil: | 40.9 |
| Oil Profile: | |
| Oleic: | 88.95 percent |
| C16:0: | 3.53 percent |
| C16:1: | 0.13 percent |
| C18:0: | 2.49 percent |
| C18:2: | 2.98 percent |
| Saturated: | 7.55 percent |
| Imidazolinone resistance: | Excellent |

In Table 7 that follows, select characteristics of OI1601A are compared with commercial variety 7350.

TABLE 7

| Trait | OI1601A | 7350 |
|---|---|---|
| Days to Flower | 68 | 64 |
| Days to Maturity | 95 | 96 |
| Height | 57 inches | 73 inches |
| Number of Leaves | 29 | 24 |
| Head Diameter | 7 inches | 8 inches |
| Seed No. per Head | 463 | 1822 |
| Seed Weight (g/200) | 12 | 10 |
| Yield (lbs/acre) | 1,125 | 3034 |

In Table 8 that follows, the oil profiles of OI1601A and commercial variety 7350 are compared.

TABLE 8

| OI1 Trait | OI1601A | 7350 |
|---|---|---|
| Total Percent Oil | 40.9 | 45.2 |
| Percent Oleic | 88.95 | 87.4 |
| Percent C16:0 | 3.53 | 3.77 |
| Percent C16:1 | 0.13 | 0.15 |
| Percent C18:0 | 2.49 | 3.11 |
| Percent C18:2 | 2.98 | 2.93 |
| Percent Saturated | 7.55 | 8.62 |

In Table 9 that follows, the imidazolinone resistances of OI1601A and commercial variety 7350 are compared using a scale of 1 to 9 where 1 is excellent resistance and 9 is poor resistance. Column 1 shows the dosage of herbicide applied and the time after application at which resistance was measured. IMI is imidazolinone herbicide, 1×IMI is one times the standard dosage of imidazolinone and so on.

TABLE 9

| Imidazolinone Resistance | OI1601A | 7350 |
|---|---|---|
| 1 week after spray | | |
| 1X IMI | 2.0 | 9.0 |
| 2X IMI | 3.0 | 9.0 |
| 3X IMI | 3.5 | 9.0 |
| 3 weeks after spray | | |
| 1X IMI | 1.0 | 9.0 |
| 2X IMI | 1.0 | 9.0 |
| 3X IMI | 1.0 | 9.0 |

Example 3

Sunflower Cultivar OI2653R Having Imidazolinone Resistance and High Oleic Acid Content A third example of imidazolinone resistance and high oleic acid content is sunflower cultivar OI2653R. OI2653R was developed through plant breeding and is stable and uniform. It is a high oleic sunflower that is resistant to imidazolinones. Some of the criteria used to select in various generations include: seed yield, lodging resistance, emergence, disease tolerance and maturity. The cultivar has shown uniformity and stability, as described in the following variety description information. It has been self-pollinated a sufficient number of generations with careful attention to uniformity of plant type. The cultivar has been increased with continued observation for uniformity. OI2653R has the following morphologic and other characteristics.

TABLE 10

| Plant: | |
|---|---|
| Height: | 62 inches |
| Number of leaves: | 24 |
| Leaf shape: | Cordate |
| Leaf length: | 11.7 inches |
| Leaf width: | 9.8 inches |
| Leaf margin indentation: | Intermediate |
| Leaf Attitude: | Descending |
| Days to Flower: | 74 |
| Days to Maturity: | 102 |
| Ray flower color: | Yellow |
| Pappi: | Green |
| Head diameter: | 4.5 inches |
| Head shape: | Flat |
| Head Attitude: | Descending |
| Percent oil: | 42.8 |
| Oil Profile: | |
| Oleic: | 89 percent |
| C16:0: | 3.4 percent |
| C16:1: | 0.11 percent |
| C18:0: | 2.26 percent |
| C18:2: | 3.26 percent |
| Saturated: | 7.15 percent |
| Imidazolinone resistance: | Excellent |

In Table 11 that follows, select characteristics of OI2653R are compared with commercial variety 7350.

TABLE 11

| Trait | OI2653R | 7350 |
|---|---|---|
| Days to Flower | 74 | 64 |
| Days to Maturity | 102 | 96 |
| Height | 62 inches | 73 inches |

TABLE 11-continued

| Trait | OI2653R | 7350 |
|---|---|---|
| Number of Leaves | 24 | 24 |
| Head Diameter | 4.5 inches | 8 inches |
| Seed No. per Head | 510 | 1822 |
| Seed Weight (g/200) | 7 | 10 |
| Yield (lbs/acre) | 400 | 3034 |

In Table 12 that follows, the oil profiles of OI2653R and commercial variety 7350 are compared.

TABLE 12

| Oil Trait | OI2653R | 7350 |
|---|---|---|
| Total Percent Oil | 42.8 percent | 45.2 percent |
| Percent Oleic | 89 | 87.4 |
| Percent C16:0 | 3.4 | 3.77 |
| Percent C16:1 | 0.11 | 0.15 |
| Percent C18:0 | 2.26 | 3.11 |
| Percent C18:2 | 3.26 | 2.93 |
| Percent Saturated | 7.15 | 8.62 |

In Table 13 that follows, the imidazolinone resistances of OI2653R and commercial variety 7350 are compared using a scale of 1 to 9 where 1 is excellent resistance and 9 is poor resistance. Column 1 shows the dosage of herbicide applied and the time after application at which resistance was measured. IMI is imidazolinone herbicide, 1×IMI is one times the standard dosage of imidazolinone and so on.

TABLE 13

| Imidazolinone Resistance | OI2653R | 7350 |
|---|---|---|
| 1 week after spray | | |
| 1X IMI | 2.0 | 9.0 |
| 2X IMI | 3.5 | 9.0 |
| 3X IMI | 3.5 | 9.0 |
| 3 weeks after spray | | |
| 1X IMI | 1.0 | 9.0 |
| 2X IMI | 1.0 | 9.0 |
| 3X IMI | 1.0 | 9.0 |

In Table 14 that follows, the FAME analysis of OI2653R is compared with that of commercial variety 7350. Each FIGURE is the percent of total fatty acid oil.

TABLE 14

| Oil Profile | OI2653R | 7350 |
|---|---|---|
| C14:0 | 0.04 | 0.05 |
| C16:0 | 3.40 | 3.77 |
| C16:1 | 0.11 | 0.15 |
| C18:0 | 2.26 | 3.11 |
| C18:1 | 89 | 87.42 |
| C18:2 | 3.26 | 2.93 |
| C18:3 | 0.11 | 0.08 |
| C20:0 | 0.26 | 0.34 |
| TOTSAT | 7.15 | 8.62 |

Example 4

Sunflower Cultivar OI1601B Having Imidazolinone Resistance and High Oleic Acid Content A fourth example of imidazolinone resistance and high oleic content is sunflower cultivar OI1601B. OI1601B was developed through plant breeding and is stable and uniform. It is a high oleic sunflower that is resistant to imidazolinones. Some of the criteria used to select in various generations include: seed yield, lodging resistance, emergence, disease tolerance and maturity. The cultivar has shown uniformity and stability, as described in the following variety description information. It has been self-pollinated a sufficient number of generations with careful attention to uniformity of plant type. The cultivar has been increased with continued observation for uniformity. OI1601B has the following morphologic and other characteristics.

TABLE 15

| Plant: | |
|---|---|
| Height: | 57 inches |
| Number of leaves: | 29 |
| Leaf shape: | Cordate |
| Leaf length: | 10.6 inches |
| Leaf width: | 10.2 inches |
| Leaf margin indentation: | Intermediate |
| Leaf Attitude: | Descending |
| Days to Flower: | 68 |
| Days to Maturity: | 95 |
| Ray flower color: | Yellow |
| Pappi: | Green |
| Head diameter: | 7 inches |
| Head shape: | Convex |
| Head Attitude: | Descending |
| Seed Number per head: | 463 |
| Seed weight (g/200): | 12 |
| Harvest moisture (percent): | 10 |
| Yield (lbs/acre): | 1,125 |
| Percent oil: | 40.9 |
| Oil Profile: | |
| Oleic: | 88.95 percent |
| C16:0: | 3.53 percent |
| C16:1: | 0.13 percent |
| C18:0: | 2.49 percent |
| C18:2: | 2.98 percent |
| Saturated: | 7.55 percent |
| Imidazolinone resistance: | Excellent |

In Table 16 that follows, the FAME analysis of OI1601B is compared with that of commercial variety 7350. Each FIGURE is the percent of total fatty acid oil.

TABLE 16

| Oil Profile | OI1601B | 7350 |
|---|---|---|
| C14:0 | 0.04 | 0.05 |
| C16:0 | 3.40 | 3.77 |
| C16:1 | 0.11 | 0.15 |
| C18:0 | 2.26 | 3.11 |
| C18:1 | 89 | 87.42 |
| C18:2 | 3.26 | 2.93 |
| C18:3 | 0.11 | 0.08 |
| C20:0 | 0.26 | 0.34 |
| TOTSAT | 7.15 | 8.62 |

This invention is also directed to methods for producing a sunflower plant by crossing a first parent sunflower plant with a second parent sunflower plant, wherein the first or second sunflower plant is the sunflower plant from the cultivar E833229, OI1601A, OI2653R, or OI1601B. Further, both first and second parent sunflower plants may be from the cultivar E833229, OI1601A, OI2653R, or OI1601B. Therefore, any methods using the cultivars E83329, OI1601A, OI2653R, or OI1601B are part of this invention: selfing, backcrosses, hybrid breeding, and crosses to populations. Any plants produced using E83329, OI1601A, OI2653R, or OI1601B as a parent are within the scope of this invention.

Useful methods include, but are not limited to, expression vectors introduced into plant tissues using a direct gene transfer method such as microprojectile-mediated delivery, DNA injection, electroporation and the like. More preferably, expression vectors are introduced into plant tissues using microprojectile delivery with a biolistic device or *Agrobacterium*-mediated transformation. Transformant plants obtained with the protoplasm of the invention are intended to be within the scope of this invention.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes." Over the last fifteen to twenty years, several methods for producing transgenic plants have been developed, and the present invention, in particular embodiments, also relates to transformed versions of the claimed variety or line.

Plant transformation involves the construction of an expression vector that will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed sunflower plants, using transformation methods as described below to incorporate transgenes into the genetic material of the sunflower plant(s).

Expression Vectors for Sunflower Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts and include, for example, genes that code for enzymes that metabolically detoxify a selective chemical agent that may be an antibiotic or an herbicide, or genes that encode an altered target that is insensitive to the inhibitor. A few positive selection methods are also known in the art.

One commonly used selectable marker gene for plant transformation is the neomycin phosphotransferase II (nptII) gene under the control of plant regulatory signals, which confers resistance to kanamycin. Fraley et al., *Proc. Natl. Acad. Sci. U.S.A.*, 80:4803 (1983). Another commonly used selectable marker gene is the hygromycin phosphotransferase gene, which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford et al., *Plant Physiol.* 86:1216 (1988); Jones et al., *Mol. Gen. Genet.*, 210:86 (1987); Svab et al., *Plant Mol. Biol.* 14:197 (1990); and Hille et al., *Plant Mol. Biol.* 7:171 (1986). Other selectable marker genes confer resistance to herbicides such as glyphosate, glufosinate or broxynil. Comai et al., *Nature* 317:741-744 (1985); Gordon-Kamm et al., *Plant Cell* 2:603-618 (1990); and Stalker et al., *Science* 242:419-423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987); Shah et al., *Science* 233:478 (1986); and Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. R. A. Jefferson, *Plant Mol. Biol. Rep.* 5:387 (1987); Teeri et al., *EMBO J.* 8:343 (1989); Koncz et al., *Proc. Natl. Acad. Sci. U.S.A.* 84:131 (1987); and DeBlock et al., *EMBO J.* 3:1681 (1984).

In vivo methods for visualizing GUS activity that do not require destruction of plant tissue are available. Molecular Probes publication 2908, Imagene Green™, p. 1-4 (1993), and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

A gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Expression Vectors for Sunflower Transformation: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissues are referred to as "tissue-specific." A "cell type"-specific promoter primarily drives expression in certain cell types in one or more organs, for example, vascular cells in roots or leaves. An "inducible" promoter is a promoter that is under environmental control. Examples of environmental conditions that may effect transcription by inducible promoters include anaerobic conditions or the presence of light. Tissue-specific, tissue-preferred, cell type-specific, and inducible promoters constitute the class of "non-constitutive" promoters. A "constitutive" promoter is a promoter that is active under most environmental conditions.

A. Inducible Promoters—An inducible promoter is operably linked to a gene for expression in sunflower. Optionally, the inducible promoter is operably linked to a nucleotide sequence encoding a signal sequence that is operably linked to a gene for expression in sunflower. With an inducible promoter, the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system, which responds to copper (Mett et al., *PNAS* 90:4567-4571 (1993)), In2 gene from maize, which responds to benzenesulfonamide herbicide safeners (Hershey et al., *Mol. Gen. Genetics* 227:229-237 (1991)), and Gatz et al., *Mol. Gen. Genetics* 243:32-38 (1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters—A constitutive promoter is operably linked to a gene for expression in sunflower or the constitutive promoter is operably linked to a nucleotide sequence encoding a signal sequence that is operably linked to a gene for expression in sunflower.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2:163-171 (1990)), ubiquitin (Christensen et al., *Plant Mol. Biol.* 12:619-632 (1989), and Christensen et al., *Plant Mol. Biol.* 18:675-689 (1992)), pEMU (Last et al., *Theor. Appl. Genet.* 81:581-588 (1991)), MAS (Velten et al., *EMBO J.* 3:2723-2730 (1984)), maize H3 histone (Lepetit et al., *Mol. Gen. Genetics* 231:276-285 (1992), and Atanassova et al., *Plant Journal* 2 (3):291-300 (1992)), *Arabidopsis* actin (Last and Gray, *Plant Mol. Biol.* 12:655-666 (1989)), and pea plastocyanin promoter (McCabe et al., *Theor. Appl. Genet.* 99:587-592 (1999)).

The ALS promoter, Xba1/NcoI fragment 5' to the *Brassica napus* ALS3 structural gene (or a nucleotide sequence similar to the Xba1/NcoI fragment), represents a particularly useful constitutive promoter. See PCT application WO 96/30530.

C. Tissue-specific or Tissue-preferred Promoters—A tissue-specific promoter is operably linked to a gene for expression in sunflower. Optionally, the tissue-specific promoter is operably linked to a nucleotide sequence encoding a signal sequence that is operably linked to a gene for expression in sunflower. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983), and Sengupta-Gopalan et al., *Proc. Natl. Acad. Sci. U.S.A.* 82:3320-3324 (1985)), a leaf-specific and light-induced promoter such as that from cab or rubisco (Simpson et al., *EMBO J.* 4(11): 2723-2729 (1985), and Timko et al., *Nature* 318:579-582 (1985)), an anther-specific promoter such as that from LAT52 (Twell et al., *Mol. Gen. Genetics* 217:240-245 (1989)), a pollen-specific promoter such as that from Zm13 (Guerrero et al., *Mol. Gen. Genetics* 244:161-168 (1993)), or a microspore-preferred promoter such as that from apg (Twell et al., *Sex. Plant Reprod.* 6:217-224 (1993)).

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., *Plant Mol. Biol.* 20:49 (1992); P. S. Close, Master's Thesis, Iowa State University (1993); C. Knox et al., "Structure and Organization of Two Divergent Alpha-Amylase Genes from Barley," *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., A short amino acid sequence able to specify nuclear location, *Cell* 39:499-509 (1984); and Steifel, et al., Expression of a maize cell wall hydroxyproline-rich glycoprotein gene in early leaf and root vascular differentiation, *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods, which are discussed, for example, by Heney and Orr, *Anal. Biochem.* 114:92-6 (1981).

According to a preferred embodiment, the transgenic plant provided for commercial production of foreign protein is a sunflower plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology*, CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance genes to engineer plants that are resistant to specific pathogen strains. See, for example, Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (*Arabidopsis* RSP2 gene for resistance to *Pseudomonas syringae*).

B. A gene conferring resistance to a pest, such as soybean cyst nematode. See, e.g., PCT Application WO 96/30517 and PCT Application WO 93/19181.

C. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, the disclosure by Van Damme et al., *Plant Molec. Biol.* 24:25 (1994), who disclose the nucleotide sequences of several *Clivia miniata* mannose-binding lectin genes.

E. A vitamin-binding protein such as avidin. See PCT application US93/06487. The application teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide that, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., *Gene* 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules that contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

L. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

M. A hydrophobic moment peptide. See PCT application WO 95/16776 (disclosure of peptide derivatives of Tachyplesin, which inhibit fungal plant pathogens) and PCT application WO 95/18855 (teaches synthetic antimicrobial peptides that confer disease resistance).

N. A membrane permease, a channel former or a channel blocker. For example, see the disclosure of Jaynes et al., *Plant Sci.* 89:43 (1993), of heterologous expression of a cecropin-β, lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., *Nature* 366:469 (1993), who show that transgenic plants expressing recombinant antibody genes are protected from virus attack.

R. A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene that encodes a bean endopolygalacturonase-inhibiting protein is described by Toubart et al., *Plant J.* 2:367 (1992).

S. A development-arrestive protein produced in nature by a plant. For example, Logemann et al., *Bio/Technology* 10:305

(1992), have shown that transgenic plants expressing the barley ribosome-inactivating gene have an increased resistance to fungal disease.

2. Genes That Confer Resistance to an Herbicide:

A. An herbicide that inhibits the growing point or meristem, such as an imidazolinone or a sulfonylurea. Exemplary genes in this category code for mutant ALS and AHAS enzymes as described, for example, by Lee et al., *EMBO J.* 7:1241 (1988), and Miki et al., *Theor. Appl. Genet.* 80:449 (1990), respectively.

B. Glyphosate (resistance impaired by mutant 5-enolpyruv1-3-phosphikimate synthase (EPSP) and aroA genes, respectively) and other phosphono compounds such as glufosinate (phosphinothricin acetyl transferase, (PAT) and *Streptomyces hygroscopicus* phosphinothricin-acetyl transferase, bar, genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSP that can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes that confer resistance to herbicides such as L-phosphinothricin. The nucleotide sequence of a phosphinothricin-acetyl-transferase gene is provided in European application No. 0 242 246 to Leemans et al., DeGreef et al., *Bio/Technology* 7:61 (1989), describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2 and Acct-S3 genes described by Marshall et al., *Theor. Appl. Genet.* 83:435 (1992).

C. An herbicide that inhibits photosynthesis, such as a triazine (psbA and gs+ genes) or a benzonitrile (nitrilase gene). Przibila et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes that Confer or Contribute to a Value-Added Trait, Such as:

A. Modified fatty acid metabolism, for example, by transforming a plant with an antisense gene of stearoyl-ACP desaturase to increase stearic acid content of the plant. See Knultzon et al., *Proc. Natl. Acad. Sci. U.S.A.* 89:2624 (1992).

B. Decreased phytate content—1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. In maize for example, this could be accomplished by cloning and then reintroducing DNA associated with the single allele that is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus* mutants fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus licheniformis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

Methods for Sunflower Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, B. R. Glick and J. E. Thompson, Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, B. R. Glick and J. E. Thompson, Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of the plant. See, for example, C. I. Kado, *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation, wherein DNA is carried on the surface of microprojectiles measuring 1 to 4 μm. The expression vector is introduced into plant tissues with a biolistic device that accelerates the microprojectiles to speeds of 300 to 600 m/s, which is sufficient to penetrate plant cell walls and membranes. Sanford et al., *Part. Sci. Technol.* 5:27 (1987), J. C. Sanford, *Trends Biotech.* 6:299 (1988), Klein et al., *Bio/Technology* 6:559-563 (1988), J. C. Sanford, *Physiol. Plant* 7:206 (1990), Klein et al., *Biotechnology* 10:268 (1992). See also U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985), and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495-1505 (1992); and Spencer et al., *Plant Mol. Biol.* 24:51-61 (1994).

Following transformation of sunflower target tissues, expression of the above-described selectable marker genes allows for preferential selection of transformed cells, tissues and/or plants, using regeneration and selection methods now well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular sunflower line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple X by Y cross, or the process of backcrossing, depending on the context.

Tissue Culture of Sunflower

Further production of the OI1601A, OI2653R and OI1601B cultivars or the E83329 hybrid can occur by self-pollination or by tissue culture and regeneration. Tissue culture of various tissues of sunflower and regeneration of plants therefrom is known. For example, the propagation of a sunflower cultivar by tissue culture is described in, but not limited to, any of the following: Shin et al., *In Vitro Cellular and Development Biology—Plant*, 36:273-278 (2000); Hildebrandt and Riker, *Amer. J. Bot.*, 34:421-427 (1947); Rogers et al., *In Vitro*, 6:463-7 (1974); Fambrini et al., *Ann. Bot.*, 92:145-152 (2003).

When the term "sunflower plant" is used in the context of the present invention, this also includes any single gene conversions of that variety. The term "single gene converted plant" as used herein refers to those sunflower plants that are developed by a plant breeding technique called backcrossing, wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental sunflower plant that contributes the gene for the desired characteristic is termed the "nonrecurrent" or "donor parent." This terminology refers to the fact that the nonrecurrent parent is used one time in the backcross protocol and, therefore, does not recur. The parental sunflower plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a sunflower plant is obtained, wherein essentially all of the desired morphological and physiological characteristics of the recurrent parent are recovered in the converted plant, in addition to the single transferred gene from the nonrecurrent parent, as determined at the 5 percent significance level when grown in the same environmental conditions.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic and, therefore, the desired physiological and morphological constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic; examples of these traits include, but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185, 5,973,234 and 5,977,445.

Further reproduction of the variety can occur by tissue culture and regeneration. Tissue culture of various tissues of sunflowers and regeneration of plants therefrom is well known and widely published. For example, reference may be had to Mayor, et al., *Plant Cell, Tissue and Organ Culture*, 72:99-103 (2003), and Baker et al., *Plant Cell, Tissue and Organ Culture*, 58:39-49 (1999). Thus, another aspect of this invention is to provide cells that, upon growth and differentiation, produce sunflower plants having the physiological and morphological characteristics of sunflower cultivars OI1601A, OI2653R, or OI1601B or the sunflower hybrid E83329.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

This invention is also directed to methods for producing a sunflower plant by crossing a first parent sunflower plant with a second parent sunflower plant, wherein the first or second parent sunflower plant is a sunflower plant of the variety OI1601A, OI2653R, or OI1601B or the hybrid E83329. Further, both first and second parent sunflower plants can come from the sunflower variety OI1601A, OI2653R, or OI1601B or the hybrid E83329. Thus, any such methods using the sunflower variety OI1601A, OI2653R, or OI1601B or the sunflower hybrid E83329 are part of this invention: selling, backcrosses, hybrid production, crosses to populations, and the like. All plants produced using sunflower variety OI1601A, OI2653R, or OI1601B or sunflower hybrid E83329, as a parent are within the scope of this invention, including those developed from varieties derived from sunflower variety OI1601A, OI2653R, or OI1601B or sunflower hybrid E83329. Advantageously, the sunflower variety may be used in crosses with other, different, sunflower plants to produce first generation ($F_1$) sunflower hybrid seeds and plants with superior characteristics. The variety of the invention may also be used for transformation where exogenous genes are introduced and expressed by the variety of the invention. Genetic variants created either through traditional breeding methods using variety OI1601A, OI2653R, or OI1601B or hybrid E83329, or through transformation of variety OI1601A, OI2653R, or OI1601B or hybrid E83329 by any of a number of protocols known to those of skill in the art are intended to be within the scope of this invention.

Deposits of the sunflower cultivars OI1601A, OI2653R, and OI1601B and of sunflower hybrid E83329 are maintained by Dow Agrosciences at Agrigenetics, Inc. d/b/a Mycogen Seeds, Highway 75 North, Breckenridge, Minnesota 56520. Access to these deposits will be available during the pendency of this application to persons determined by the Commissioner of Patents and Trademarks to be entitled thereto under 37 CFR 1.14 and 35 USC 122. Upon allowance of any claims in this application, all restrictions on the availability to the public of these varieties will be irrevocably removed by affording access to deposits of at least 2,500 seeds of each of the same varieties with the American Type Culture Collection, Manassas, Va.

While a number of exemplary aspects and embodiments have been discussed above, those of skill in the art will recognize certain modifications, permutations, additions and sub-combinations thereof. It is, therefore, intended that the following appended claims and claims hereafter introduced are interpreted to include all such modifications, permutations, additions and sub-combinations as are within their true spirit and scope.

What is claimed is:

1. A seed of sunflower cultivar OI1601A, a representative sample of seed of the cultivar having been deposited under ATCC Accession No. PTA-9470.

2. A sunflower plant, or a part thereof, produced by growing the seed of claim 1.

3. A tissue culture of regenerate cells produced from the plant of claim 2.

4. A sunflower plant regenerated from the tissue culture of claim 3 wherein the plant has all the morphological and physiological characteristics of cultivar OI1601A.

5. A method for producing a hybrid sunflower seed wherein the method comprises crossing the plant of claim 2 with a different sunflower plant and harvesting the resultant hybrid sunflower seed.

6. A method of introducing a desired trait into sunflower cultivar OI1601A wherein the method comprises:
   (a) crossing an OI1601A plant, representative seed having been deposited under ATCC Accession No. PTA-9470, with a plant of another sunflower cultivar that comprises a desired trait to produce progeny plants wherein the desired trait is selected from the group consisting of male sterility, herbicide resistance, insect resistance, and resistance to bacterial disease, fungal disease or viral disease;
   (b) selecting progeny plants that have the desired trait to produce selected progeny plants;
   (c) crossing the selected progeny plants with the OI1601A plants to produce backcross progeny plants;
   (d) selecting for backcross progeny plants that have the desired trait and physiological and morphological characteristics of sunflower cultivar OI1601A to produce selected backcross progeny plants; and
   (e) repeating steps (c) and (d) one or more times in succession to produce selected second or higher backcross progeny plants that comprise the desired trait and all of the physiological and morphological characteristics of sunflower cultivar OI1601A as determined at the 5 percent significance level when grown in the same environmental conditions.

7. A plant produced by the method of claim 6 wherein the plant has the desired trait and all of the physiological and morphological characteristics of sunflower cultivar OI1601A as determined at the 5 percent significance level when grown in the same environmental conditions.

8. A seed of sunflower cultivar OI2653R, a representative sample of seed of the cultivar having been deposited under ATCC Accession No. PTA-9472.

9. A sunflower plant, or a part thereof, produced by growing the seed of claim 8.

10. A tissue culture of regenerable cells produced from the plant of claim 9.

11. A sunflower plant regenerated from the tissue culture of claim 10 wherein the plant has all the morphological and physiological characteristics of cultivar OI2653R.

12. A method for producing a hybrid sunflower seed wherein the method comprises crossing the plant of claim 9 with a different sunflower plant and harvesting the resultant hybrid sunflower seed.

13. A method of introducing a desired trait into sunflower cultivar OI2653R wherein the method comprises:
   (a) crossing an OI2653R plant, representative seed having been deposited under ATCC Accession No. PTA-9472, with a plant of another sunflower cultivar that comprises a desired trait to produce progeny plants wherein the desired trait is selected from the group consisting of male sterility, herbicide resistance, insect resistance, and resistance to bacterial disease, fungal disease or viral disease;
   (b) selecting progeny plants that have the desired trait to produce selected progeny plants;
   (c) crossing the selected progeny plants with the OI2653R plants to produce backcross progeny plants;
   (d) selecting for backcross progeny plants that have the desired trait and physiological and morphological characteristics of sunflower cultivar OI2653R to produce selected backcross progeny plants; and
   (e) repeating steps (c) and (d) one or more times in succession to produce selected second or higher backcross progeny plants that comprise the desired trait and all of the physiological and morphological characteristics of sunflower cultivar OI2653R as determined at the 5 percent significance level when grown in the same environmental conditions.

14. A plant produced by the method of claim 13 wherein the plant has the desired trait and all of the physiological and morphological characteristics of sunflower cultivar OI2653R as determined at the 5 percent significance level when grown in the same environmental conditions.

15. A seed of sunflower cultivar OI1601B, a representative sample of seed of the cultivar having been deposited under ATCC Accession No. PTA-9471.

16. A sunflower plant, or a part thereof, produced by growing the seed of claim 15.

17. A tissue culture of regenerable cells produced from the plant of claim 16.

18. A sunflower plant regenerated from the tissue culture of claim 17 wherein the plant has all the morphological and physiological characteristics of cultivar OI1601B.

19. A method for producing a hybrid sunflower seed wherein the method comprises crossing the plant of claim 16 with a different sunflower plant and harvesting the resultant hybrid sunflower seed.

20. A method of introducing a desired trait into sunflower cultivar OI1601B wherein the method comprises:
   (a) crossing an OI1601B plant, representative seed having been deposited under ATCC Accession No. PTA-9471, with a plant of another sunflower cultivar that comprises a desired trait to produce progeny plants wherein the desired trait is selected from the group consisting of male sterility, herbicide resistance, insect resistance, and resistance to bacterial disease, fungal disease or viral disease;
   (b) selecting progeny plants that have the desired trait to produce selected progeny plants;
   (c) crossing the selected progeny plants with the OI1601B plants to produce backcross progeny plants;
   (d) selecting for backcross progeny plants that have the desired trait and physiological and morphological characteristics of sunflower cultivar OI1601B to produce selected backcross progeny plants; and
   (e) repeating steps (c) and (d) one or more times in succession to produce selected second or higher backcross progeny plants that comprise the desired trait and all of the physiological and morphological characteristics of sunflower cultivar OI1601B as determined at the 5 percent significance level when grown in the same environmental conditions.

21. A plant produced by the method of claim 20 wherein the plant has the desired trait and all of the physiological and morphological characteristics of sunflower cultivar OI1601B as determined at the 5 percent significance level when grown in the same environmental conditions.

22. A seed of sunflower hybrid E83329, a representative sample of seed of the cultivar having been deposited under ATCC Accession No. PTA-9473.

23. A sunflower plant, or a part thereof, produced by growing the seed of claim 22.

24. A tissue culture of regenerable cells produced from the plant of claim 23.

25. A sunflower plant regenerated from the tissue culture of claim 24 wherein the plant has all the morphological and physiological characteristics of cultivar E83329.

26. A method for producing a hybrid sunflower seed wherein the method comprises crossing the plant of claim 23 with a different sunflower plant and harvesting the resultant hybrid sunflower seed.

27. A method of introducing a desired trait into sunflower cultivar E83329 wherein the method comprises:
   (a) crossing an E83329 plant, representative seed having been deposited under ATCC Accession No. PTA-9473, with a plant of another sunflower cultivar that comprises a desired trait to produce progeny plants wherein the desired trait is selected from the group consisting of male sterility, herbicide resistance, insect resistance, and resistance to bacterial disease, fungal disease or viral disease;
   (b) selecting progeny plants that have the desired trait to produce selected progeny plants;
   (c) crossing the selected progeny plants with the E83329 plants to produce backcross progeny plants;
   (d) selecting for backcross progeny plants that have the desired trait and physiological and morphological characteristics of sunflower cultivar E83329 to produce selected backcross progeny plants; and
   (e) repeating steps (c) and (d) one or more times in succession to produce selected second or higher backcross progeny plants that comprise the desired trait and all of the physiological and morphological characteristics of sunflower cultivar E83329 as determined at the 5 percent significance level when grown in the same environmental conditions.

28. A plant produced by the method of claim 27 wherein the plant has the desired trait and all of the physiological and morphological characteristics of sunflower cultivar E83329 as determined at the 5 percent significance level when grown in the same environmental conditions.

29. A process for producing an oil comprising an oleic acid content of greater than 85 percent, the process comprising the steps of:
   (a) providing a sunflower seed having a gene for resistance to imidazolinone herbicide and an oleic acid content of greater than 85 percent, wherein the resistance gene is a gene which confers tolerance to imidazolinone, wherein the sunflower seed is seed of sunflower cultivar OI1601A and wherein a representative sample of seed of the cultivar was deposited under ATCC Accession No. PTA-9470, and
   (b) recovering the oil comprising an oleic acid content of greater than 85 percent.

30. A process for producing an oil comprising an oleic acid content of greater than 85 percent, the process comprising the steps of:
   (a) providing a sunflower seed having a gene for resistance to imidazolinone herbicide and an oleic acid content of greater than 85 percent, wherein the resistance gene is a gene which confers tolerance to imidazolinone, wherein the sunflower seed is seed of sunflower cultivar OI2653R and wherein a representative sample of seed of the cultivar was deposited under ATCC Accession No. PTA-9472, and
   (b) recovering the oil comprising an oleic acid content of greater than 85 percent.

31. A process for producing an oil comprising an oleic acid content of greater than 85 percent, the process comprising the steps of:
   (a) providing a sunflower seed having a gene for resistance to imidazolinone herbicide and an oleic acid content of greater than 85 percent, wherein the resistance gene is a gene which confers tolerance to imidazolinone, wherein the sunflower seed is seed of sunflower cultivar OI1601B and wherein a representative sample of seed of the cultivar was deposited under ATCC Accession No. PTA-9471, and
   (b) recovering the oil comprising an oleic acid content of greater than 85 percent.

32. A process for producing an oil comprising an oleic acid content of greater than 85 percent, the process comprising the steps of:
   (a) providing a sunflower seed having a gene for resistance to imidazolinone herbicide and an oleic acid content of greater than 85 percent, wherein the resistance gene is a gene which confers tolerance to imidazolinone, wherein the sunflower seed is seed of sunflower cultivar E83329 and wherein a representative sample of seed of the cultivar was deposited under ATCC Accession No. PTA-9473, and (b) recovering the oil comprising an oleic acid content of greater than 85 percent.

* * * * *